United States Patent
Jensen

(10) Patent No.: US 12,102,640 B2
(45) Date of Patent: *Oct. 1, 2024

(54) USE OF DOPAMINE AND SEROTONIN RECEPTOR ANTAGONISTS FOR TREATMENT IN A SUBJECT WITH RETINAL DEGENERATION

(71) Applicant: United States Government as represented by the Department of Veterans Affairs, Washington, DC (US)

(72) Inventor: Ralph Jensen, Washington, DC (US)

(73) Assignee: United States Government as represented by the Department of Veterans Affairs, Washington, DC (US)

(*) Notice: Subject to any disclaimer, the term of this patent is extended or adjusted under 35 U.S.C. 154(b) by 194 days.

This patent is subject to a terminal disclaimer.

(21) Appl. No.: 17/322,871

(22) Filed: May 17, 2021

(65) Prior Publication Data

US 2021/0267999 A1   Sep. 2, 2021

Related U.S. Application Data

(63) Continuation of application No. 15/218,774, filed on Jul. 25, 2016, now Pat. No. 11,033,554.

(60) Provisional application No. 62/196,805, filed on Jul. 24, 2015.

(51) Int. Cl.
| | |
|---|---|
| *A61K 31/5513* | (2006.01) |
| *A61K 9/00* | (2006.01) |
| *A61K 31/40* | (2006.01) |
| *A61K 31/4439* | (2006.01) |
| *A61K 31/444* | (2006.01) |
| *A61K 31/445* | (2006.01) |
| *A61K 31/451* | (2006.01) |
| *A61K 31/454* | (2006.01) |
| *A61K 31/496* | (2006.01) |

(52) U.S. Cl.
CPC ........ *A61K 31/5513* (2013.01); *A61K 9/0048* (2013.01); *A61K 9/0051* (2013.01); *A61K 31/40* (2013.01); *A61K 31/4439* (2013.01); *A61K 31/444* (2013.01); *A61K 31/445* (2013.01); *A61K 31/451* (2013.01); *A61K 31/454* (2013.01); *A61K 31/496* (2013.01)

(58) Field of Classification Search
CPC .................................................. A61K 31/5513
See application file for complete search history.

(56) References Cited

U.S. PATENT DOCUMENTS

| | | | |
|---|---|---|---|
| 4,624,957 A | 11/1986 | Schachar | |
| 4,886,795 A | 12/1989 | Schachar | |
| 4,886,815 A | 12/1989 | Schachar | |
| 11,033,554 B2 * | 6/2021 | Jensen | ................... A61K 31/40 |
| 2003/0207943 A1 | 11/2003 | Mueller | |
| 2008/0137036 A1 | 6/2008 | Bedell | |

OTHER PUBLICATIONS

U.S. Appl. No. 62/196,805, filed Jul. 24, 2015, Ralph Jensen.
U.S. Appl. No. 15/218,774, now U.S. Pat. No. 11,033,554, filed Jul. 25, 2016, Ralph Jensen.
Chen, et al. (2012) "Mechanisms of All-trans-retinal Toxicity with Implications for Standard Disease and Age-Related Macular Degeneration," *Journal of Biol. Chem.*, 287(7) pp. 5059-5069.
Chen, et al. (2013) "Systems Pharmacology Identifies Drug Targets for Stargardt Disease- Associated Retinal Degeneration," *Journal of Clinical Investigation*, 123(12) 16 pages.
Cuenca, et al. (2004) "Regressive and Reactive Changes in the Connectivity Patterns of Rod and Cone Pathways of P23H Transgenic Rat Retina" *Neuroscience*, 127, pp. 301-317.
Fornaro, et al. (2002) "Pathogenesis of Degenerative Retinopathies Induced by Thioridazine and Other Antipsychotics: a Dopamine Hypothesis," *Documenta Ophthalmologica*, 105, pp. 41-49.
Hess-Rover, et al. (1999) "Diagnosis and Treatment of a Severe Psychotic Illness in a Man with Dual Severe Sensory Impairments Caused y the Presence of Usher Syndrome," *Journal of Intell. Disab. Res.* 43 (5) pp. 428-434.
Jensen, et al. (1986) "Effects of Dopamine and Its Agonists and Antagonists on the Receptive Field Properties of Ganglion Cells in the Rabbit Retina," *Neuroscience*, 17 (3), pp. 837-855.
Jensen, et al. (1988) "Effects of Dopaminergic Agents on the Activity of Ganglion Cells in the Rabbit Retina", *Dopaminergic Mechanisms in Vision*, pp. 163-177.
Klien, et al. (2012) "Genetics of Parkinson's Disease," *Cold Springs Harb Perspect Med*, a008888, pp. 1-15.
NIH National Eye Institute "Facts About Retinitis Pigmentosa," https://nei.nih.gov/health/pigmentosa/pigmentosa_facts, accessed May 25, 2018.
Machida, et al. (2000) "P23H Rhodopsin Transgenic Rat: Correlation of Retinal Function with Histopathology," *Invest. Ophthalmol. Vis. Sci.*, 41 (10), pp. 3200-3209.
Noue-Matsuhisa, et al. (2003) "Effect of MCI-9042, a 5-HT2 Receptor Antagonist, on Retinal Ganglion Cell Death and Retinal Ischemia," *Experimental Eye Research*, 76, pp. 445-452.
Ogilvia, et al. (2009) "Dopamine Receptor Loss of Function is Not Protective of rd1 Rod Photoreceptors in Vivo," *Mol. Vision*, 15, pp. 2868-2878.
Raymond, et al. (2014), "Efficacy of Electrical Stimulation of Retinal Ganglion Cells with Temporal Patterns Resembling Light-Evoked Spike Trains," Conf. Proc IEEE Eng. Bed. Biol. Soc, pp. 1707-1710.
Tullis, et al. (2015) "Sarpogrelate, a 5-HT2a Receptor Antagonist, Protects the Retinal From Light-Induced Retinopathy," *Invest. Opthal. & Visual Sci.*, 56 (8) 10 pages.

\* cited by examiner

*Primary Examiner* — Rei Tsang Shiao
(74) *Attorney, Agent, or Firm* — Ballard Spahr LLP

(57) ABSTRACT

Disclosed herein are methods of treating disorders of the retina (e.g., macular degeneration, retinitis pigmentosa, etc.) comprising administering to a subject in need of such treatment a therapeutically effective amount of a compound (for example, an antipsychotic drug) that blocks or diminishes agonist-mediated responses upon binding to either dopamine D2-like receptors or serotonin 5-HT2 receptors.

20 Claims, 4 Drawing Sheets

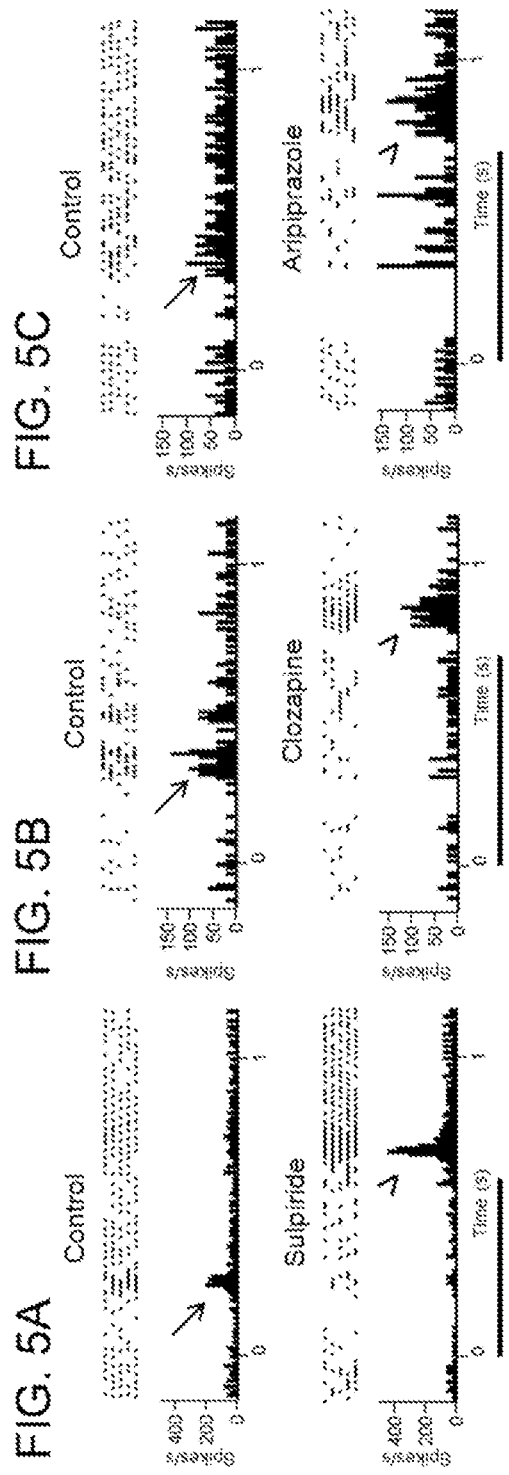

USE OF DOPAMINE AND SEROTONIN RECEPTOR ANTAGONISTS FOR TREATMENT IN A SUBJECT WITH RETINAL DEGENERATION

RELATED APPLICATION

The present application is a continuation of U.S. application Ser. No. 15/218,774, filed Jul. 25, 2016, which claims priority to U.S. Application No. 62/196,805, filed Jul. 24, 2015, the contents of which are herein incorporated by reference in their entireties.

GOVERNMENT RIGHTS

The U.S. Government has a paid-up license in this invention and the right in limited circumstances to require the patent owner to license others on reasonable terms as provided for by the terms of the Merit Review Award 1 I01 RX001299 awarded by the Department of Veterans Affairs.

BACKGROUND

Field of the Invention

The present invention pertains to uses of compounds acting at dopamine D2-like receptors and/or serotonin 5-HT2 receptors for treating a subject with retinal degeneration.

Related Art

Photoreceptor degeneration is a leading cause of blindness in people worldwide. Retinitis pigmentosa (RP) is one of the most common forms of hereditary retinal degeneration. RP represents a group of related genetic eye disorders that clinically manifest in both non-syndromic forms involving isolated visual disability as well as syndromic forms involving other organs or tissues, such as Usher Disease or Bardet-Biedl syndrome, which manifests both in the retina and in the cochlea of the ear. In most cases of RP the disorder leads first to night blindness, and subsequently progressive loss of peripheral and central vision. Age-related macular degeneration (AMD) is a degenerative acquired retinal disorder caused by a complex interplay of genetic and environmental factors. As its name implies, the disease affects specifically the macula, which is the central retina, while the peripheral retina is spared for the most part. Therefore peripheral visual field is usually preserved even in late stages of the disease. Treatment options for RP and AMD remain limited. Retinal prostheses are being used in advanced stages of RP and anti-VEGF medicines are being used to slow vision loss for neovascular ("wet" or exudative) AMD, a form of AMD. Other, therapeutic approaches are generally restricted to slowing down the degenerative process by sunlight protection and vitamin therapy, treating complications (such as cataract and macular edema), and helping patients to cope with the social and psychological impact of blindness. There exists the need for pharmaceutical products to effectively treat patients with retinal degeneration.

SUMMARY

The present invention provides methods for treating a disorder or disease of the retina, comprising administration to a subject in need of thereof, a therapeutic effective amount of one or more compounds that block or diminish stimulation of dopamine D2-like receptors or serotonin 5-HT2 receptors. In some embodiments, the methods include selecting a subject with retinal degeneration and administrating a dopamine D2-like receptor antagonist, a dopamine D2-like receptor partial agonist, or a dopamine D2-like receptor inverse agonist to the subject. In other embodiments, the methods include selecting a subject with retinal degeneration and administering a serotonin 5-HT2 receptor antagonist, a serotonin 5-HT2 receptor partial agonist, or a serotonin 5-HT2 receptor inverse agonist to the subject. In other embodiments, the methods include a subject with retinal degeneration and administrating a compound that blocks or diminishes stimulation of both dopamine D2-like receptors and serotonin 5-HT2 receptors to the subject. In one non-limiting example, the compound is an antipsychotic drug.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which:

FIG. 5A shows the effects of 12 UM sulpiride on the light responses of a long-latency ON-center P23H rat RGC. Spike raster plots and PSTHs of spike activity recorded from the RGC are displayed. Sulpiride eliminated the ON response (indicated by arrow) and brought out an OFF response (indicated by arrowhead). Horizontal bar indicates the timing and duration of the light stimulus.

FIG. 5B shows the effects of 5 μM clozapine on the light responses of a long-latency ON-center P23H rat RGC. Spike raster plots and PSTHs of spike activity recorded from the RGC are displayed. Clozapine eliminated the ON response (indicated by arrow) and brought out an OFF response (indicated by arrowhead). Horizontal bar indicates the timing and duration of the light stimulus.

FIG. 5C shows the effects of 5 μM aripiprazole on the light responses of a long-latency ON-center P23H rat RGC. Spike raster plots and PSTHs of spike activity recorded from the RGC are displayed. Aripiprazole did not eliminate the ON response (indicated by arrow) but brought out an OFF response (indicated by arrowhead). Horizontal bar indicates the timing and duration of the light stimulus.

DETAILED DESCRIPTION

Figure 1A:
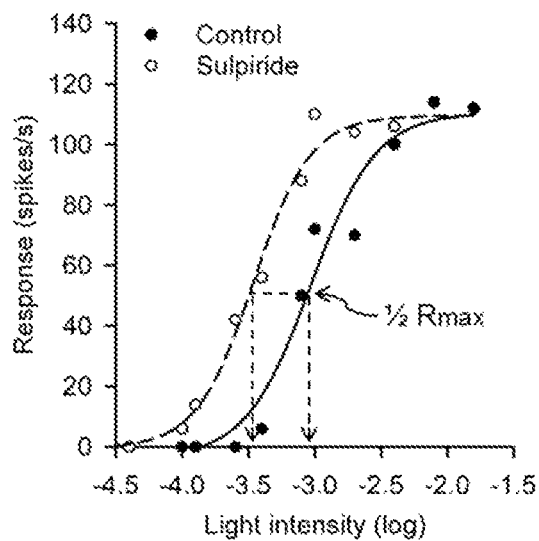
FIG. 1A shows that 13 UM sulpiride shifted the intensity-response curve from a P23H rat RGC to the left. The abscissa is labeled as log-unit attenuation in stimulus intensity from the maximum ($8.5 \times 10^{17}$ photons/cm$^2$/s).

Certain embodiments disclosed herein provide for treating a disorder or disease of the retina. For example, one method disclosed herein allows for administering to a subject a therapeutically effective amount of one or more compounds that block or diminish stimulation of dopamine D2-like receptors or serotonin 5-HT2 receptors. After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

In retinal diseases such as RP and AMD, loss of vision arises from degeneration or malfunction of retinal cells. Consequently, normal neuronal transmission along the visual pathway is disrupted in the affected parts of the visual field. One strategy to remedy this loss of function would be to enhance the visual neurotransmission in the retina to compensate for the region of impairment. The retina contains receptors for many neurotransmitters, including dopamine and serotonin. Accumulated experimental evidence from normal, healthy animals indicates that retinal dopamine increases signal flow through cone circuits and decreases signal flow through rod circuits (Documenta Ophthalmology 108: 17-40, 2004). Less is known of the possible function of serotonin in the retina, although serotonin 5-HT1A receptor agonists have been reported to protect the retina from severe photo-oxidative stress (Investigative Ophthalmology & Visual Science 52: 2118-2126, 2011). As disclosed herein, diminishing or blocking the activity at dopamine D2-like and/or serotonin 5-HT2 receptors improves light responses of retinal neurons in an animal model of retinal degeneration.

As disclosed herein, a compound that blocks or diminishes stimulation of dopamine D2-like receptors or serotonin 5-HT2 receptors improves the light-evoked responses in a rat model of retinal degeneration. Ocular administration of dopamine D2-like receptor or serotonin 5-HT2 receptor antagonists, for example, by intraocular administration (such as intravitreal injection), subconjunctival injection, or topical administration, presents a promising therapy for individuals with RP, AMD, or other retinal degenerations where vision has diminished. The dopamine D2-like or serotonin 5-HT2 receptor antagonists may also be administered systemically (for example, intravenously or orally). Partial agonists or inverse agonists of dopamine D2-like or serotonin 5-HT2 receptor may also be used, either ocularly or systemically, to diminish or block receptor activity.

I. Abbreviations

AMD age-related macular degeneration
L-745,870 3-(4-[4-Chlorophenyl]piperazin-1-yl)-methyl-1-H-pyrrolo[2,3-b]pyridinetrihydrochloride
MDL-100907 (R)-(+)-α-(2,3-Dimethoxyphenyl)-[1-[2-(4-fluorophenyl)ethyl]-4-piperinemethanol, Volinanserin
PSTH peristimulus time histogram
RGC retinal ganglion cell
RP retinitis pigmentosa
SB-242084 6-Chloro-2,3-dihydro-5-methyl-N-[6-[(2-methyl-3-pyridinyl)oxy]-3-pyridinyl]-1H-indole-1-carboxyamide dihydrochloride
SD Sprague-Dawley

II. Terms

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. As used herein, "comprises" means "includes." Thus, "comprising A or B," means "including A, B, or A and B," without excluding additional elements. All publications, patent applications, patents, and other references mentioned herein are incorporated by reference in their entirety for all purposes.

Although methods and materials similar or equivalent to those described herein can be used in the practice or testing of the present disclosure, suitable methods and materials are described below. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Antagonist: a type of receptor ligand or drug that blocks or dampens agonist-mediated responses. The term "antagonist", as used herein, is defined in the broad sense, comprising competitive antagonists, non-competitive antagonists, uncompetitive antagonists, neutral (silent) antagonists, partial agonists, inverse agonists, and negative allosteric modulators. Such antagonists may be, for example, small organic molecules, peptides, polypeptides, fusion proteins, antibodies, antibody fragments, mimetibodies or polynucleotides.

Partial agonist: a type of receptor ligand that binds to and activates a given receptor, but has only partial efficacy at the receptor relative to a full agonist. When both a full agonist and partial agonist are present, the partial agonist acts as an antagonist, competing with the full agonist for receptor occupancy and producing a net decrease in the receptor activation observed with the full agonist alone.

Inverse agonist: a type of receptor ligand that binds to the same receptor as an agonist but induces a pharmacological response opposite to that agonist. A prerequisite for an inverse agonist response is that the receptor must have a constitutive (also known as intrinsic or basal) level activity in the absence of any ligand.

Antipsychotic drug: is a compound that is generally used to treat psychotic symptoms. Psychotic symptoms can be part of conditions such as schizophrenia, schizoaffective disorder, personality disorder and bipolar disorder. Antipsychotic drugs are commonly classified as first-generation (or typical) and second-generation (or atypical) antipsychotics. First-generation antipsychotic drugs may also be used for the treatment of acute mania, agitation, and other conditions. These drugs can cause extra pyramidal motor control disabilities in patients. These drugs have a high affinity for the D2-like family of dopamine receptors. Some examples of first-generation antipsychotics include: chlorpromazine, flupentixol, haloperidol, levomepromazine, pericyazine, perphenazine, pimozide, sulpiride, trifluoperazine, and zuclopenthixol. Second-generation antipsychotic drugs may also be used for the treatment of depression, bipolar and acute mania. Compared to first-generation antipsychotic, these are less likely to cause extra pyramidal motor control disabilities in the patient. In general, these drugs are potent 5-HT2 receptor antagonists and relatively weaker dopamine D2-like antagonists. Some examples of second generation antipsychotics include: amisulpride, aripiprazole, clozapine, olanzapine, quetiapine, risperidone and sertindole.

Age-related macular degeneration (AMD): A condition in which the cells of the macula (the central part of the retina) degenerate, resulting in loss of central visual acuity. AMD is the most common cause of irreversible loss of central vision and legal blindness in the elderly. It causes progressive damage to the macula, resulting in gradual loss of central vision. There are two forms, atrophic and neovascular macular degeneration. In atrophic degeneration (dry form), the tissues of the macula thin as photoreceptor cells disappear. There is currently no treatment for atrophic degeneration, though dietary supplements may help slow progression. In neovascular macular degeneration (wet form), abnormal blood vessels develop under the macula. These vessels may leak fluid and blood under the retina and eventually a mound of scar tissue develops under the retina. Central vision becomes washed out and loses detail, and straight lines may appear wavy. For neovascular macular degeneration there are some treatments available, including the use of medication injected directly into the eye (e.g., anti-VEGF therapy), laser therapy in combination with a targeting drug (e.g., photodynamic therapy) and brachytherapy. However, repeated treatments can cause complications leading to loss of vision.

Effective amount: A dose or quantity of a specified compound sufficient to induce a desired response or result, for example to inhibit advancement, or to cause regression of a disease or disorder, or which is capable of relieving one or more symptoms caused by the disease. The preparations disclosed herein are administered in effective amounts. In some examples, this can be the amount or dose of a disclosed dopamine D2-like or serotonin 5-HT2 receptor antagonist required to improve vision in a subject, such as a subject with a retinal degeneration. In one embodiment, a therapeutically effective amount is the amount that alone, or together with one or more additional therapeutic agents (such as additional agents for treating a retinal disorder), induces the desired response, such as improved vision in the subject.

Dopamine D2-like receptor: Dopamine is the major catecholamine neurotransmitter present in the mammalian retina. Dopamine receptors can be divided into two classes (D1-like and D2-like) on the basis of their biochemical and physiological effects (Missale et al. Physiol. Rev. 78: 189-225, 1998). The D1-like receptors include D1 and D5 receptors, and the D2-like receptors include D2, D3 and D4 receptors.

Serotonin 5-HT2 receptor: 5-Hydroxytryptamine (5-HT, serotonin) is a monoamine neurotransmitter synthesized from L-tryptophan. 5-HT acts at serotonin receptors, which have been classified into seven groups (5-HT1-7) based on their pharmacological profiles and signal transduction mechanisms (Nichols and Nichols, Chem. Rev., 108: 1614-1641, 2008). Except for the 5-HT3 receptor, which is a ligand-gated ion channel, 5-HT receptors belong to the G-protein-coupled receptor superfamily. The 5-HT1, 5-HT2, 5-HT3 and 5-HT5 receptor groups have been further subdivided. Three subtypes of 5-HT2 receptors have been identified: 5-HT2A, 5-HT2B and 5-HT2C.

Pharmaceutically acceptable carriers: The pharmaceutically acceptable carriers useful in this disclosure are conventional. Remington: The Science and Practice of Pharmacy, 22nd Edition (London: Pharmaceutical Press, 2012), describes compositions and formulations suitable for pharmaceutical delivery of the compounds disclosed herein. In general, the nature of the carrier will depend on the particular mode of administration being employed.

Retinal degeneration: Deterioration of the retina, including progressive death of the photoreceptor cells of the retina or associated structures (such as retinal pigment epithelium). Retinal degeneration includes diseases or conditions such as retinitis pigmentosa, cone-rod dystrophy, macular degeneration (such as age-related macular degeneration and Stargardt-like macular degeneration), and maculopathies.

Retinal ganglion cell (RGC): A neuron located in the ganglion cell layer of the retina. RGCs receive neural inputs from amacrine cells and/or bipolar cells (which themselves receive neural input from photoreceptor cells). The axons of RGCs form the optic nerve, which transmits information from the retina to the brain.

Improve vision: Enhancing visual function in at least one of the following categories: visual acuity, visual fields, color vision, contrast sensitivity, dark adaptation, light adaptation, navigation and orientation. Examples of measurable specific tasks of visual function include motion discrimination, spatial detection, object counting, form discrimination, and object identification.

Retinitis pigmentosa (RP): A group of inherited retinal disorders that eventually lead to partial or complete blindness, characterized by progressive loss of photoreceptor cell function. Symptoms of RP include progressive peripheral vision loss and night vision problems (nyctalopia) that can eventually lead to central vision loss. RP is caused by mutations in over 100 different genes, and is both genotypically and phenotypically heterogeneous. Approximately 30% of RP cases are caused by a mutation in the rhodopsin gene. The pathophysiology of RP predominantly includes cell death of rod photoreceptors; however, some forms affect cone photoreceptors or the retinal pigment epithelium (RPE). Typical clinical manifestations include bone spicules, optic nerve waxy pallor, atrophy of the RPE in the mid periphery of the retina, retinal arteriolar attenuation, bull's eye maculopathy, and peripheral retinal atrophy.

Subject: Living multi-cellular vertebrate organisms, a category that includes both human and non-human mammals.

III. Use of Dopamine and Serotonin Receptor Antagonists for Improving Vision Disclosed herein are methods of improving vision in a subject with retinal degeneration. The methods include administering a compound that blocks or diminishes activity at dopamine D2-like receptors and/or serotonin 5-HT2 receptors.

In some embodiments, the methods include selecting a subject (such as human subject) with retinal degeneration and administering a dopamine D2-like receptor antagonist to the subject. In other embodiments, the methods include selecting a subject (such as human subject) with retinal degeneration and administering a serotonin 5-HT2 receptor antagonist to the subject. In other embodiments, the methods include selecting a subject (such as human subject) with retinal degeneration and administering an antipsychotic drug to the subject. In particular embodiments, the retinal degeneration is in a particular portion of the retina, for example in the macula and/or fovea (as in macular degeneration) or in the peripheral retina (as in RP). In some embodiments, the methods further include measuring vision improvement in the subject. In some examples, vision in the subject is improved, for example as compared to a control.

Methods for measuring or assessing visual function in a subject are well known to one of skill in the art. See, e.g., Kanski and Bowling, Clinical Ophthalmology: A Systematic Approach, 7th Edition, Elsevier, 2011; Carlson and Kurtz, Clinical Procedures for Ocular Examination, 3rd Edition, McGraw-Hill Medical, Inc, 2003; Liu, Volpe and Galetta, Neuro-Ophthalmology: Diagnosis and Management, 2nd Edition, Elsevier, 2010. In some examples, methods for measuring or assessing visual function include detecting an electrical response of the retina to a light stimulus. In some examples, the response is detected by measuring an electroretinogram (ERG; for example full-field ERG, multifocal ERG, pattern ERG, or ERG photostress test), visual evoked potential, or optokinetic nystagmus (see, e.g., Wester et al., Invest. Ophthalmol. Vis. Sci. 48:4542-4548, 2007). In other examples, visual function is measured by directly detecting retinal response (for example by use of a microelectrode at the retinal surface). In further examples, visual function can be measured by exposing the subject to light stimuli (for example one or more pulses of light) and asking the subject to report detection of the stimulus, for example orally or by pushing a button, closing a switch, or other similar reporting means. The intensity of the light stimulus can be increased or decreased to measure a light sensitivity threshold. For example, visual function is measured by determining the intensity threshold, which is the minimum luminance of a test spot required to produce a visual sensation (perception) or electrical response of the retina. This can be measured by placing a subject in a dark or light room and increasing the luminance of a test spot until the subject reports its presence or an electrical response is detected. The test spot can be a focal spot of light directed at a fixed location on the retina, for example the fovea or a location in the peripheral retina.

In some embodiments of the disclosed methods, improved vision in a subject includes an increase in one or more measures of retinal response, for example about a 10% to a 100-fold or more increase (such as at least about a 10% 20%, 30%, 40%, 50%, 60%, 70%, 80%, 90%, 1.5-fold, 2-fold, 3-fold, 5-fold, 10-fold, 20-fold, 30-fold, 40-fold, 50-fold, 60-fold, 70-fold, 80-fold, 90-fold, 95-fold, 100-fold increase, or more) in the subject as compared to a control. In some examples, improved vision in a subject includes an increase in the number, size (amplitude), dynamic range, and/or frequency of an electrical response by the retina to one or more light stimuli as compared to a control. In other examples, improved vision also includes a decreased threshold for stimulation of an electrical response to a light stimulus, for example, a detectable response or a response of a particular magnitude is evoked at a lower light intensity as compared to a control. In further examples, improved vision includes a decreased threshold for stimulation of a visible signal in response to a light stimulus, for example, a visible signal that is detectable (reported) by the subject is evoked at a lower light intensity as compared to a control. In a particular example, the change is detected in the intensity threshold. In yet other embodiments, more global measurements of visual function are used, such as an improvement in visual acuity (for example, measured on a Snellen chart), at least a partial restoration of a visual field deficit (for example, measured on a Humphrey Field Analyzer of Nidek microperimeter), such as a decrease in the size of a central visual field deficit of the type seen in macular degeneration or a peripheral visual field deficit as seen in RP, improvement in contrast sensitivity, or improvement in flicker sensitivity.

The control can be any suitable control against which to compare visual function or retinal function of a subject. In some embodiments, the control is a reference value or ranges of values. For example, in some examples, the reference value is derived from the average values obtained from a group of subjects with a retinal degeneration (such as the same or a different retinal disorder as the subject), for example, an untreated subject or a subject treated with vehicle alone. In other examples, the control is obtained from the same subject, for example, a subject with retinal degeneration prior to treatment. In further examples, the reference value can be derived from the average values obtained from a group of normal control subjects (for example, subjects without a retinal degeneration).

In some embodiments, the methods include selecting a subject with retinal degeneration. In some examples, the subject is a mammalian subject (such as a human subject or a primate or rodent subject). A subject with retinal degeneration can be identified utilizing standard diagnostic methods, including but not limited to, measuring or assessing visual function, retinal function, and/or retinal structure of the subject, such as visual acuity, visual field, ERG, Amsler grid, fundus examination, color vision, fluorescein angiography, optical coherence tomography, or a combination of two or more thereof. In some examples, a retinal degeneration includes retinitis pigmentosa (RP), Usher syndrome, Stargardt's disease, cone-rod dystrophy, Leber congenital amaurosis, a retinopathy (such as diabetic retinopathy), a maculopathy (for example, age-related macular degeneration (AMD), Stargardt-like macular degeneration, vitelliform macular dystrophy (Best disease), Malattia Leventinese (Doyne's honeycomb retinal dystrophy), diabetic maculopathy, occult macular dystrophy, or cellophane maculopathy), congenital stationary night blindness, degenerative myopia, or damage associated with laser therapy (for example, grid, focal, or panretinal), including photodynamic therapy.

It is to be understood that dopamine D2-like receptor antagonists for use in the present disclosure include any known dopamine D2-like receptor antagonists and also include novel dopamine D2-like receptor antagonists developed in the future.

It is to be understood that serotonin 5-HT2 receptor antagonists for use in the present disclosure include any known serotonin 5-HT2 receptor antagonists and also include novel serotonin 5-HT2 receptor antagonists developed in the future.

IV. Modes of Administration

Pharmaceutical compositions that include one or more of the inhibitors of dopamine D2-like or serotonin 5-HT2 signaling disclosed herein can be formulated with an appropriate solid or liquid carrier, depending upon the particular mode of administration chosen. The pharmaceutically acceptable carriers and excipients useful in this disclosure are conventional. See, e.g., Remington: The Science and Practice of Pharmacy, 22nd Edition (London: Pharmaceutical Press, 2012).

For instance, parenteral formulations usually include injectable fluids that are pharmaceutically and physiologically acceptable fluid vehicles such as water, physiological saline, other balanced salt solutions, aqueous dextrose, glycerol or the like. For solid compositions {e.g., powder, pill, tablet, or capsule forms), conventional nontoxic solid carriers can include, for example, pharmaceutical grades of mannitol, lactose, starch, or magnesium stearate. In addition to biologically-neutral carriers, pharmaceutical compositions to be administered can contain minor amounts of nontoxic auxiliary substances, such as wetting or emulsifying agents, preservatives, pH buffering agents, or the like, for example sodium acetate or sorbitan monolaurate. Excipients that can be included are, for instance, proteins, such as human serum albumin or plasma preparations.

The dosage form of the pharmaceutical composition will be determined by the mode of administration chosen. For instance, in addition to injectable fluids, topical, inhalation, oral and intraocular formulations can be employed. Topical preparations can include eye drops, ointments, sprays, patches and the like. Inhalation preparations can be liquid (e.g., solutions or suspensions) and include mists, sprays and the like. Oral formulations can be liquid (e.g., syrups, solutions or suspensions), or solid (e.g., powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those skilled in the art.

In some examples, the pharmaceutical composition may be administered by any means that achieve their intended purpose. Amounts and regimens for the administration of the selected dopamine D2-like or serotonin 5-HT2 receptor antagonists will be determined by the attending clinician. Effective doses for therapeutic application will vary depending on the nature and severity of the condition to be treated, the particular compound(s) selected, the age and condition of the patient, and other clinical factors. Typically, the dose range will be from about 0.001 mg/kg body weight to about 500 mg/kg body weight. Other suitable ranges include doses of from about 0.01 mg/kg to 1 mg/kg, about 0.1 mg/kg to 30 mg/kg body weight, about 1 mg/kg to 100 mg/kg body weight, or about 10 mg/kg to about 50 mg/kg. The dosing schedule may vary from once a week to daily or multiple times per day, depending on a number of clinical factors, such as the subject's sensitivity to the compound. Examples of dosing schedules are about 1 mg/kg administered twice a week, three times a week or daily; a dose of about 10 mg/kg twice a week, three times a week or daily; or a dose of about 100 mg/kg twice a week, three times a week or daily.

The pharmaceutical compositions that include one or more of the disclosed inhibitors of dopamine D2-like or serotonin 5-HT2 signaling can be formulated in unit dosage form, suitable for individual administration of precise dosages. In one specific, non-limiting example, a unit dosage can contain from about 1 ng to about 500 mg of a dopamine D2-like or serotonin 5-HT2 receptor antagonist (such as about 1 ng to 10 ng, about 100 ng to 1 µg, about to 10 µg to 100 µg, about 1 mg to 10 mg, or about 100 mg to 500 mg). The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated. In some examples, the dopamine D2-like or serotonin 5-HT2 receptor antagonist is administered daily, weekly, bi-weekly, or monthly. In other examples, the dopamine D2-like or serotonin 5-HT2 receptor antagonist is administered one or more times a day, such as once, twice, three, or four times daily.

The compounds of this disclosure can be administered to humans or other animals on whose tissues they are effective in various manners such as topically, orally, intravenously, intramuscularly, intraperitoneally, intranasally, intradermally, intrathecally, subcutaneously, intraocularly, via inhalation, or via suppository. In one example, the compounds are administered to the subject topically. In another example, the compounds are administered to the subject intraocularly (for example intravitreally). In some examples, the amount of compound is sufficient to result in a vitreal concentration of about 1 nM to 500 µM (such as about 1 nM to 10 nM, about to 100 nM to 1 µM, about 10 µM to 100 µM, or about 200 µM to 500 µM). In further examples, the compounds are administered orally or intravenously. The particular mode of administration and the dosage regimen will be selected by the attending clinician, taking into account the particulars of the case (e.g., the particular dopamine D2-like or serotonin 5-HT2 receptor antagonist, the subject, the disease, the disease state involved, and whether the treatment is prophylactic). Treatment can involve monthly, bi-monthly, weekly, daily or multi-daily doses of compound(s) over a period of a few days to months, or even years.

In some embodiments, the disclosed dopamine D2-like or serotonin 5-HT2 receptor antagonists can be included in an inert matrix for either topical application or injection into the eye, such as for intravitreal administration. As one example of an inert matrix, liposomes may be prepared from dipalmitoyl phosphatidylcholine (DPPC), such as egg phosphatidylcholine (PC). Liposomes, including cationic and anionic liposomes, can be made using standard procedures as known to one skilled in the art. Liposomes including one or more dopamine D2-like and/or serotonin 5-HT2 receptor antagonists can be applied topically, either in the form of drops or as an aqueous based cream or gel, or can be injected intraocularly (such as by intravitreal injection). In a formulation for topical application, the compound is slowly released over time as the liposome capsule degrades due to wear and tear from the eye surface. In a formulation for intraocular injection, the liposome capsule degrades due to cellular digestion. Both of these formulations provide advantages of a slow release drug delivery system, allowing the subject to be exposed to a substantially constant concentration of the compound over time. In one example, the compound can be dissolved in an organic solvent such as DMSO or alcohol as previously described and contain a polyanhydride, poly(glycolic) acid, poly(lactic) acid, or polycaprolactone polymer.

The dopamine D2-like or serotonin 5-HT2 receptor antagonists can be included in a delivery system that can be implanted at various sites in the eye, depending on the size, shape and formulation of the implant, and the type of transplant procedure. The delivery system is then introduced into the eye. Suitable sites include but are not limited to the anterior chamber, anterior segment, posterior chamber, posterior segment, vitreous cavity, suprachoroidal space, subconjunctiva, episcleral, intracorneal, epicorneal and sclera.

In one example, the delivery system is placed in the anterior chamber of the eye. In another example, the delivery system is placed in the vitreous cavity. In some examples, administering the dopamine D2-like or serotonin 5-HT2 receptor antagonist includes contacting the retina or cells of the retina (for example, one or more photoreceptors, bipolar cells, horizontal cells, amacrine cells, or RGCs) with the antagonist.

In some examples, an effective amount of a dopamine D2-like receptor antagonist can be the amount of a dopamine D2-like receptor antagonist (such as haloperidol or sulpiride) necessary to improve vision in a subject with retinal degeneration (such as RP or AMD). In some examples, an effective amount of a serotonin 5-HT2 receptor antagonist can be the amount of a serotonin 5-HT2 receptor antagonist (such as clozapine, risperidone, olanzapine, mianserin, ritanserin, mirtazapine, MDL-100907, or SB-242084) necessary to improve vision in a subject with retinal degeneration (such as RP or AMD). In some examples, an effective amount of an antipsychotic medication can be the amount of an antipsychotic medication (such as Clozaril®, Abilify® or Haldol®) necessary to improve vision in a subject with retinal degeneration (such as RP or AMD). The present disclosure also includes combinations of one or more of the disclosed dopamine D2-like and/or serotonin 5-HT2 receptor antagonists with one or more other agents useful in the treatment of a retinal degeneration. For example, the compounds of this disclosure can be administered in combination with effective doses of one or more therapies for retinal disorders, including but not limited to optopharmacology therapy, gene therapy (including optogenetic therapy), stem cell therapy, retinal prosthesis, vitamin or mineral supplements (such as vitamins A, C, and/or E, or zinc and/or copper), anti-angiogenic therapy (such as ranibizumab or bevacizumab), photocoagulation, photodynamic therapy, lutein or zeaxanthin, corticosteroids, or immunosuppressants. Appropriate combination therapy for a particular disease can be selected by one of skill in the art. For example, the dopamine D2-like and/or serotonin 5-HT2 receptor antagonists of this disclosure can be administered in combination with an antiangiogenic therapy, such as an anti-VEGF antibody (for example, bevacizumab or ranibizumab), an anti-VEGF nucleic acid (for example pegaptanib), or a VEGFR inhibitor (such as lapatinib, sunitinib, or sorafenib), to a subject with age-related macular degeneration. The term "administration in combination" or "co-administration" refers to both concurrent and sequential administration of the active agents.

The following examples are provided to illustrate certain particular features and/or embodiments. These examples should not be construed to limit the disclosure to the particular features or embodiments described.

EXAMPLES

Example 1

Sulpiride Increases Retinal Light Sensitivity
Materials and Methods
Animals and Tissue Preparation:

P23H-line 1 homozygous rats (age range 22-37 weeks) were used. Breeding pairs of P23H-line 1 homozygous rats were generously donated by Dr. Matthew LaVail (University of California San Francisco, CA). The room light was kept on a 12 hr light/dark cycle using standard fluorescent lighting. During the light cycle, the illumination at the level of the cages was 100-200 lux.

On the day of an experiment, a rat was euthanized with sodium pentobarbital (150 mg/kg, i.p.), and the eyes were removed and hemisected under normal room light. After removal of the vitreous humour from each eye, one eyecup was transferred to a holding vessel containing bicarbonate-buffered Ames medium (Sigma-Aldrich), which was continuously gassed at room temperature with 5% $CO_2$/95% $O_2$. The retina of the other eyecup was gently peeled from the retinal pigment epithelium/choroid and trimmed into a square of ~12 $mm^2$. The retina was then placed photoreceptor side down in a small volume (0.1 ml) chamber. The chamber was mounted on a fixed-stage upright microscope (Nikon Eclipse E600FN), and the retina superfused at 1.5 ml/min with bicarbonate-buffered Ames medium supplemented with 2 mg/ml D-(+) glucose and equilibrated with 5% $CO_2$/95% $O_2$. An in-line heating device (Warner Instruments) was used to maintain recording temperature at 35-36° C. The retina of the other eyecup was used later in the day.

Electrical Recording: Action potentials (spikes) were recorded extracellularly from individual RGCs. With the aid of red light (>630 nm) that was delivered from below the chamber, the tip of a glass insulated platinum/tungsten microelectrode (0.6-1.0 MΩ impedance; Thomas Recording GmbH, Germany) was visually advanced to the retinal surface with a motor-driven micromanipulator. Extracellular potentials from RGCs were amplified and bandpass filtered at 100 to 5000 Hz by a differential amplifier (Xcell-3; FHC, Bowdoin, ME). To ensure that recordings were made from single cells, the recorded waveform of the spike was continuously displayed in real time on a PC to check for uniformity of spike size and shape. Spikes from single RGCs were converted to standard transistor to transistor logic (TTL) pulses with a time-amplitude window discriminator (APM Neural Spike Discriminator, FHC). A laboratory data acquisition system (1401 Processor and Spike2 software; Cambridge Electronic Design Ltd., Cambridge, UK) was used to digitize the TTL pulses and raw spike train data.

Light Stimulation:

Light from a mercury arc lamp illuminated an aperture that was focused on the retina from above, through the 4x objective of the microscope. The image produced on the retina was either a 250-µm or 1.5-mm diameter spot, which was centered on the recorded RGC. In the light path was a 545 nm interference filter (bandwidth, 30 nm). The intensity of the unattenuated light stimulus on the retina, measured with a spectroradiometer (ILT900-R, International Light Technologies), was $8.5 \times 10^{17}$ photons/$cm^2$/s. Light intensities are expressed herein in log units relative to the unattenuated light intensity. An electromechanical shutter (Uniblitz, Rochester, NY) was used to control the stimulus duration, which was set to 100 ms in constructing intensity response curves. During recordings from RGCs, light flashes were presented with interstimulus intervals of 3-15 s (depending upon the duration and intensity of the light stimulus) to avoid any adapting effect of the previous flash. All experiments were performed in a dimly lighted room (10 lux).

Drug Application:

(−)-Sulpiride was purchased from Tocris Bioscience (Minneapolis, MN). Sulpiride was dissolved in a small amount of dimethylsulphoxide (DMSO) and diluted in physiological saline. The drug solution was applied to the bathing solution using a calibrated syringe pump (Razel Scientific Instruments). Drug was bath applied for ~10 min to ensure stable responses before effects were examined. Only one cell was studied in each retina to avoid possible residual drug effects.

Data Analysis:

Intensity-response curves were generated from the responses of RGCs to 100 ms flashes of light. The light stimulus was either a 250-µm or 1.5-mm diameter spot. The light responses of RGCs were calculated by counting the number of spikes within a 100 ms window that encompassed the peak response and subtracting any spontaneous activity, measured between light stimuli. Cell responses were averaged from 5 stimulus presentations. Intensity-response curves of RGCs were fitted with a sigmoidal dose response (variable slope), using SigmaPlot 10.0 (SPSS, Chicago, IL). Drug-induced change in light sensitivity was determined by comparing the light intensity that evoked a half-maximum response prior to drug application with the light intensity that evoked the same peak response in the presence of the drug. Numerical data are expressed as the mean±standard deviation. Statistical significance was carried out using two-tailed paired Student's t-tests (SigmaStat 3.5 software), with $P<0.05$ considered significant. Some RGCs were stimulated with both 250-µm and 1.5-mm diameter spots. Since drug-induced changes in light sensitivity in those RGCs that were stimulated with both sized spots of light did not reveal significant differences, data from both spots were averaged.

Results

The effects of the dopamine D2-like receptor antagonist sulpiride on the intensity response functions of 9 P23H rat RGCs were examined.

FIG. 1A shows the effect of sulpiride on a representative P23H rat RGC that was stimulated with a spot of light. The light intensity that evoked a half-maximum response (½ Rmax) prior to application of sulpiride was −3.03 log units attenuation. With application of sulpiride, the light intensity that evoked the same response was −3.47 log units attenuation. Therefore, sulpiride increased the light sensitivity of this cell by 0.44 log unit.

Figure 1B:
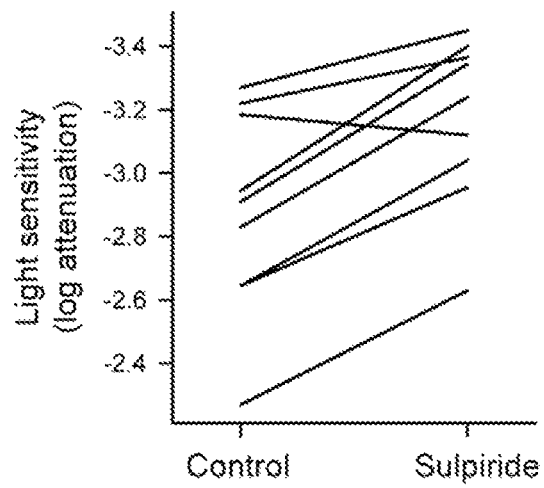
FIG. 1B shows data illustrating sulpiride-induced change in light sensitivity of P23H rat RGCs (n=9). The lines connect individual RGCs before and during drug treatment. The ordinate is labeled as log-unit attenuation in stimulus intensity from the maximum ($8.5 \times 10^{17}$ photons/cm$^2$/s).

Sulpiride increased the sensitivity of 8 of the 9 P23H rat RGCs tested (FIG. 1B). The light intensity that generated a half-maximum response prior to application of sulpiride was on average −2.88±0.33 log units attenuation. In the presence of sulpiride, the same light-evoked response was obtained at a light intensity of −3.17±0.27 log units attenuation (0.29 log unit lower intensity). The difference of the means was statistically significant ($P<0.001$; paired t-test).

Example 2

L-745,870 Increases Retinal Light Sensitivity

Experiments similar to those described in Example 1 were carried out on retinas isolated from P23H rats.

Figure 2A:
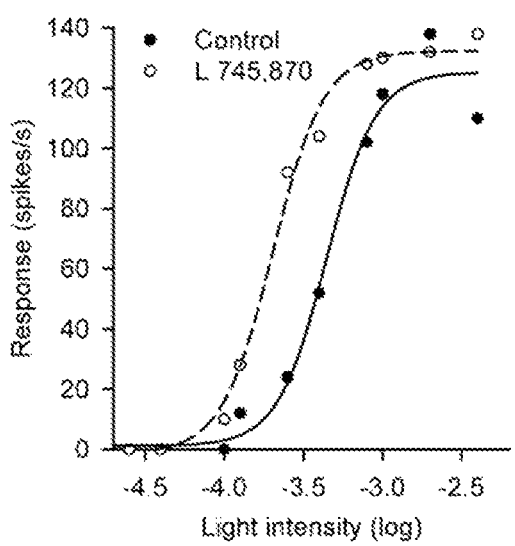
FIG. 2A shows that 1 UM L-745,870 shifted the intensity-response curve from a P23H rat RGC to the left. The abscissa is labeled as log-unit attenuation in stimulus intensity from the maximum ($8.5 \times 10^{17}$ photons/cm$^2$/s).

L-745,870 was purchased from Tocris Bioscience (Minneapolis, MN) and dissolved in physiological saline (0.9% NaCl). As in Example 1, the drug solution was applied to the bathing solution using calibrated syringe pumps (Razel Scientific Instruments). Drug was bath applied for ~10 min to ensure stable responses before effects were examined. Only one cell was studied in each retina to avoid possible residual drug effects. The effects of L-745,870, a dopamine D2-like receptor antagonist that is selective for D4 receptor (Patel et al., J. Pharmacol. and Exp. Ther. 1997, 283: 636-647), on the intensity-response functions of 12 P23H rat RGCs were examined. FIG. 2A shows the effect of L-745, 870 on a representative P23H rat RGC that was stimulated with a spot of light. The light intensity that evoked a half-maximum response prior to application of L-745,870 was −3.35 log units attenuation. With application of L-745,870, the light intensity that evoked the same response was −3.69 log units attenuation. Therefore, L-745,870 increased the light sensitivity of this cell by 0.34 log unit.

Figure 2B:
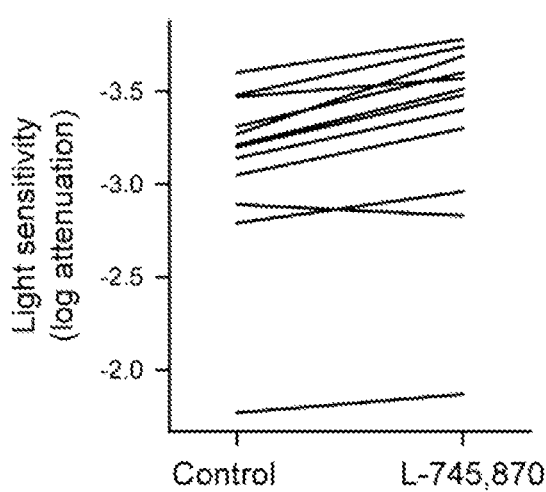
FIG. 2B shows data illustrating L-745,870-induced change in light sensitivity of P23H rat RGCs (n=12). The lines connect individual RGCs before and during drug treatment. The ordinate is labeled as log-unit attenuation in stimulus intensity from the maximum ($8.5 \times 10^{17}$ photons/cm$^2$/s).

L-745,870 increased the sensitivity of 11 of the 12 P23H rat RGCs tested (FIG. 2B). The light intensity that generated a half-maximum response prior to application of L-745,870 was on average −3.10±0.48 log units attenuation. In the presence of L-745,870, the same light-evoked response was obtained at a light intensity of −3.31±0.54 log units attenuation (0.21 log unit lower intensity). The difference of the means was statistically significant (P<0.001; paired t-test).

Example 3

Haloperidol, Amisulpride, Clozapine and Aripiprazole Increase Retinal Light Sensitivity Experiments similar to those described in Example 1 were carried out on retinas isolated from P23H rats.

Haloperidol, amisulpride, and clozapine were purchased from Tocris Bioscience (Minneapolis, MN). Aripiprazole was purchased from Sigma-Aldrich (St. Louis, MO). Haloperidol, amisulpride, and clozapine were dissolved in a small amount of dimethylsulphoxide (DMSO) and diluted in physiological saline (0.9% NaCl). Aripiprazole was dissolved in a small amount of 1 mM HCl and diluted in physiological saline. As in Example 1, the drug solutions were applied to the bathing solution using calibrated syringe pumps (Razel Scientific Instruments). Drugs were bath applied for ~10 min to ensure stable responses before effects were examined. Only one cell was studied in each retina to avoid possible residual drug effects.

Figure 3A:
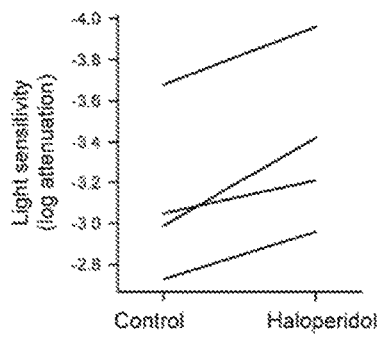
FIG. 3A is a plot showing haloperidol-induced change in light sensitivity of P23H rat RGCs (n=4). The lines connect individual RGCs before and during drug treatment. The ordinate is labeled as log-unit attenuation in stimulus intensity from the maximum ($8.5 \times 10^{17}$ photons/cm$^2$/s).

The effects of haloperidol, a D4 receptor antagonist and a D2/D3 inverse agonist (Burstein et al., J. Pharmacol and Exp Ther. 315: 1278-1287, 2005), on the intensity response functions of 4 P23H rat RGCs were examined. FIG. 3A shows that haloperidol increased the sensitivity of all 4 P23H rat RGCs. The light intensity that generated a half-maximum response prior to application of haloperidol was on average −3.11±0.40 log units attenuation. In the presence of haloperidol, the same light-evoked response was obtained at a light intensity of −3.39±0.43 log units attenuation (0.28 log unit lower intensity). The difference of the means was statistically significant (P=0.017; paired t-test).

Figure 3B:
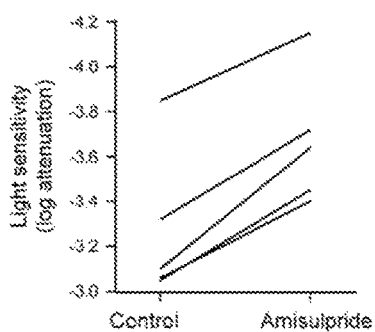
FIG. 3B is a plot showing amisulpride-induced change in light sensitivity of P23H rat RGCs (n=5). The lines connect individual RGCs before and during drug treatment. The ordinate is labeled as log-unit attenuation in stimulus intensity from the maximum ($8.5 \times 10^{17}$ photons/cm$^2$/s).

The effects of amisulpride, a D2-like receptor antagonist (Schoemaker et al., J Pharmacol & Exp Ther 280: 83-97, 1997), were examined on the intensity-response functions of 5 P23H rat RGCs. FIG. 3B shows that amisulpride increased the sensitivity of all 5 P23H rat RGCs. The light intensity that generated a half-maximum response prior to application of amisulpride was on average −3.28±0.34 log units attenuation. In the presence of amisulpride, the same light-evoked response was obtained at a light intensity of −3.67±0.30 log units attenuation (0.39 log unit lower intensity). The difference of the means was statistically significant (P<0.001; paired t-test).

Figure 3C:
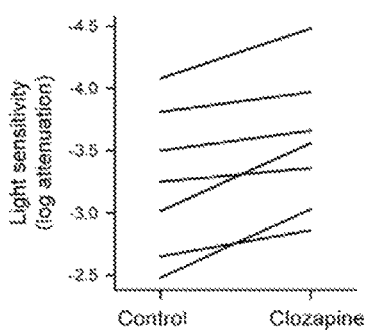
FIG. 3C is a plot showing clozapine-induced change in light sensitivity of P23H rat RGCs (n=7). The lines connect individual RGCs before and during drug treatment. The ordinate is labeled as log-unit attenuation in stimulus intensity from the maximum ($8.5 \times 10^{17}$ photons/cm$^2$/s).

The effects of clozapine, which is a D4 receptor antagonist (Seeman et al., Neuropsychopharmacology 16: 93-110, 1997) and an inverse agonist at D2/D3 receptors (Burstein et al., J Pharmacol & Exp Ther 315: 1278-1287, 2005) and 5-HT2A/2C receptors (Weiner et al., J Pharmacol & Exp Ther 299: 268-276, 2001; Herrick-Davis et al., J Pharmacol & Exp Ther 295: 226-232, 2000), were examined on the intensity-response functions of 7 P23H rat RGCs. FIG. 3C shows that clozapine increased the sensitivity of all 7 P23H rat RGCs. The light intensity that generated a half-maximum response prior to application of clozapine was on average −3.26±0.59 log units attenuation. In the presence of clozapine, the same light-evoked response was obtained at a light intensity of −3.56±0.55 log units attenuation (0.30 log unit lower intensity). The difference of the means was statistically significant (P=0.005; paired t-test).

Figure 3D:
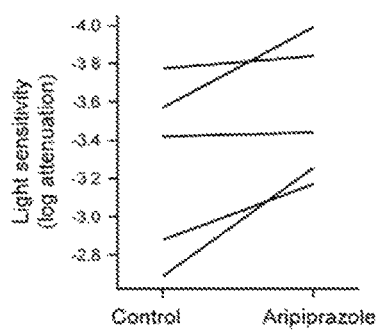
FIG. 3D is a plot showing aripiprazole-induced change in light sensitivity of P23H rat RGCs (n=5). The lines connect individual RGCs before and during drug treatment. The ordinate is labeled as log-unit attenuation in stimulus intensity from the maximum ($8.5 \times 10^{17}$ photons/cm$^2$/s).

The effects of aripiprazole, a partial agonist at D2-like and 5-HT2C receptors and an antagonist at 5-HT2A receptors (Davies et al., CNS Drug Reviews 10: 317-336, 2004), were examined on the intensity-response functions of 5 P23H rat RGCs. FIG. 3D shows the effect of aripiprazole on the light sensitivity of the P23H rat RGCs. The light intensity that generated a half-maximum response prior to application of aripiprazole was on average −3.27±0.46 log units attenuation. In the presence of aripiprazole, the same light-evoked response was obtained at a light intensity of −3.54±0.36 log units attenuation (0.27 log unit lower intensity). The difference of the means almost reached statistical significance (P<0.058; paired t-test).

Example 4

Sulpiride, Clozapine and Aripiprazole Transform Atypical ON-Center RGCs into OFF-Center RGCs Experiments similar to those described in Example 1 were carried out on retinas isolated from P23H rats.

Figure 4A:
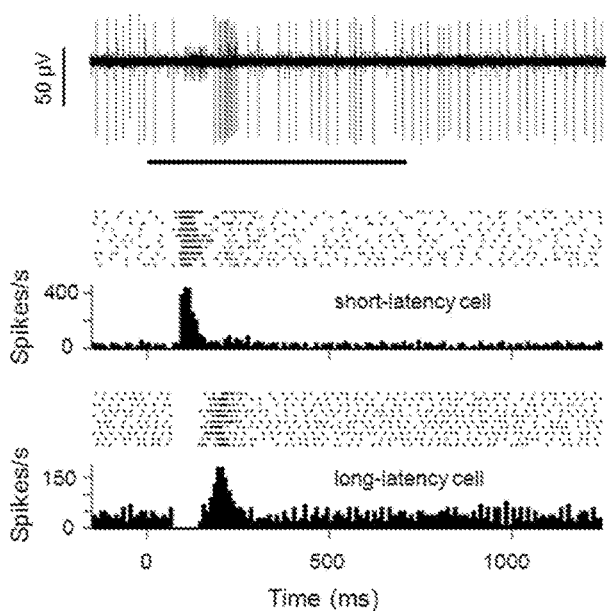
FIG. 4A shows the light responses of two types of ON-center P23H rat RGC. Top: extracellular recording of the responses from both a short-latency ON-center RGC and a long-latency ON-center RGC to a 700 ms flash of light (timing indicated by the horizontal bar). Bottom: spike raster plots and peristimulus time histograms (PSTHs) of spike activity recorded from the two RGCs.

(−)-Sulpiride and clozapine were purchased from Tocris Bioscience (Minneapolis, MN). Aripiprazole was purchased from Sigma-Aldrich (St. Louis, MO). Sulpiride and clozapine were dissolved in a small amount of dimethylsulphoxide (DMSO) and diluted in physiological saline. Aripiprazole was dissolved in a small amount of 1 mM HCl and diluted in physiological saline. As in Example 1, the drug solutions were applied to the bathing solution using calibrated syringe pumps (Razel Scientific Instruments). Drugs were bath applied for ~10 min to ensure stable responses before effects were examined. Only one cell was studied in each retina to avoid possible residual drug effects. P23H rat RGCs were identified as either ON-center or OFF-center cells from their responses to a 500-700 ms flash of a small (250-μm diameter) spot of light centered over the receptive field. ON-center cells elicit an excitatory response to the onset but not to the offset of the spot of light, whereas OFF-center cells elicit an excitatory response to the offset of the spot of light. Accordingly, it was determined that two classes of ON-center P23H rat RGC could be distinguished based on the latency of the response to light onset. FIG. 4A shows an extracellular recording where both types of ON-center cell were recorded simultaneously to stimulation with a small spot (250-μm diameter) of light. The small-amplitude spiking cell responded with a 65 ms burst of spikes, beginning 90 ms after light onset, while the large-amplitude spiking cell responded with a 60 ms burst of spikes, beginning 170 ms after light onset. Note the cessation of spike activity of the large-amplitude spiking cell immediately following the onset of light, during the time when the short-latency ON-center cell had the transient peak in activity. This reduction in spike activity can also be appreciated in the bottom raster plot and peristimulus time histogram (PSTH). A reduction in spike activity at light onset was a consistent finding among long-latency ON-center cells.

Figure 4B:
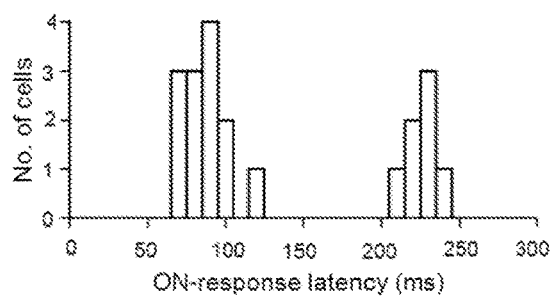
FIG. 4B shows the distribution of response latencies from ON-center P23H rat RGCs (n=20). Response latencies of RGCs were measured from 100 ms flashes of light that evoked a maximum or near-maximum peak response. Response latency was defined as the time after light onset to the peak firing frequency (10 ms bin width).

FIG. 4B shows the distribution of response latencies of 20 ON-center P23H rat RGCs. Of these, 7 cells showed a long-latency response. The distribution of response latencies of P23H rat RGCs was clearly bimodal. On average, the latency of the short-latency ON responses was 86.9±14.4 ms, and the latency of the long-latency ON responses was 226±9.8 ms.

FIG. 5A shows the effects of sulpiride on a long-latency ON-center P23H rat RGC. The RGC was stimulated with a small (250-µm diameter) spot of light. Timing and duration of the light stimulus is indicated by the horizontal line. The long-latency ON response (indicated by the arrow) to the small spot of light was abolished by sulpiride and an OFF response (indicated by the arrowhead) appeared.

FIG. 5B shows the effects of clozapine on a long-latency ON-center P23H rat RGC. The RGC was stimulated with a small (250-µm diameter) spot of light. Timing and duration of the light stimulus is indicated by the horizontal line. The long-latency ON response (indicated by the arrow) to the small spot of light was markedly reduced by clozapine, and an OFF response (indicated by the arrowhead) appeared.

FIG. 5C shows the effects of aripiprazole on a long-latency ON-center P23H rat RGC. The RGC was stimulated with a small (250-µm diameter) spot of light. Timing and duration of the light stimulus is indicated by the horizontal line. Although a long-latency ON response (indicated by the arrow) to the small spot of light was still present in the presence of aripiprazole, an OFF response (indicated by the arrowhead) now appeared. Since long-latency ON-center RGCs are uncommon in normal, healthy retinas, the long-latency ON-center RGCs in P23H rat retinas are likely a consequence of changes that are taking place in the course of retinal degeneration. It is likely that these P23H rat RGCs were at one time OFF-center cells early in the disease process.

Example 5

Sulpiride and Aripiprazole Diminish Long-Latency ON Responses in OFF-Center RGCs Experiments similar to those described in Example 1 were carried out on retinas isolated from P23H rats.

(−)-Sulpiride was purchased from Tocris Bioscience (Minneapolis, MN). Aripiprazole was purchased from Sigma-Aldrich (St. Louis, MO). Sulpiride was dissolved in a small amount of dimethylsulphoxide (DMSO) and diluted in physiological saline. Aripiprazole was dissolved in a small amount of 1 mM HCl and diluted in physiological saline. As in Example 1, the drug solutions were applied to the bathing solution using calibrated syringe pumps (Razel Scientific Instruments). Drugs were bath applied for ~10 min to ensure stable responses before effects were examined. Only one cell was studied in each retina to avoid possible residual drug effects.

Figure 6A:
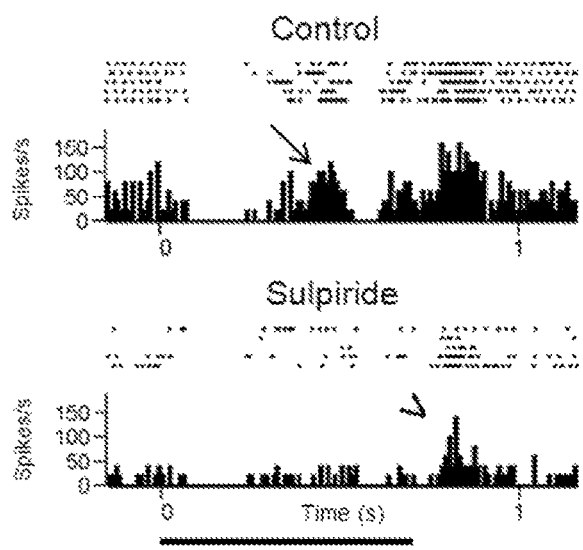
FIG. 6A shows the effects of 9 UM sulpiride on the light responses of an OFF-center P23H rat RGC. Spike raster plots and PSTHs of spike activity recorded from the RGC are displayed. Sulpiride diminished the delayed ON response (indicated by the arrow) but spared the OFF response (indicated by arrowhead). Horizontal bar indicates the timing and duration of the light stimulus.
Figure 6B:
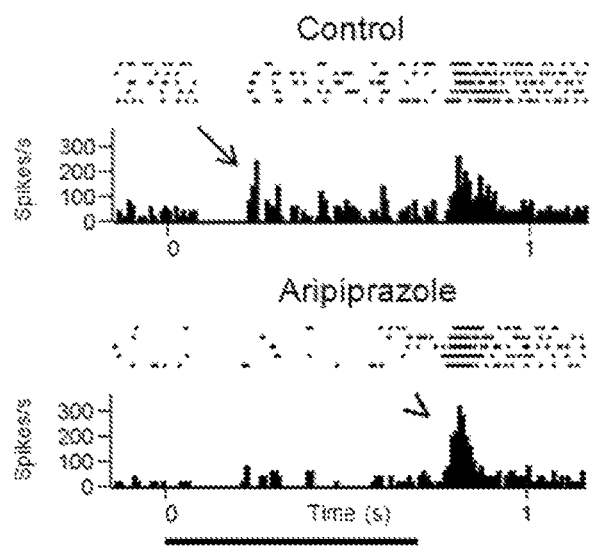
FIG. 6B shows the effects of 5 UM aripiprazole on the light responses of an OFF-center P23H rat RGC. Spike raster plots and PSTHs of spike activity recorded from the RGC are displayed. Aripiprazole eliminated the delayed ON response (indicated by the arrow) but spared the OFF response (indicated by arrowhead). Horizontal bar indicates the timing and duration of the light stimulus.

I observed that some OFF-center P23H rat RGCs showed a long-latency ON response when stimulated with a small (250-µm diameter) spot of light. Long-latency ON responses in OFF-center RGCs are rarely observed in normal, healthy retinas. Two such cells are shown in FIG. 6A and FIG. 6B. The arrows in these two figures indicate the long-latency ON responses. When the retinas exposed to either sulpiride or aripiprazole, the ON responses in these RGCs were reduced whereas the OFF responses (indicated by the arrowheads) remained intact.

Example 6

Eticlopride Improves Light Responses of RGCs

Experiments similar to those described in Example 1 were carried out on retinas isolated from P23H rats.

(−)-Eticlopride was purchased from Tocris Bioscience (Minneapolis, MN). Eticlopride was dissolved in physiological saline (0.9% NaCl). As in Example 1, the drug solution was applied to the bathing solution using calibrated syringe pumps (Razel Scientific Instruments). Drug was bath applied for ~10 min to ensure stable responses before effects were examined. Only one cell was studied in each retina to avoid possible residual drug effects.

Figure 7A:
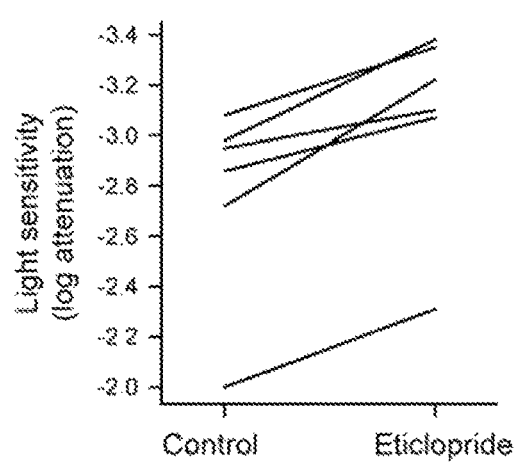
FIG. 7A shows data illustrating eticlopride-induced change in light sensitivity of P23H rat RGCs (n=6). The lines connect individual RGCs before and during drug treatment. The ordinate is labeled as log-unit attenuation in stimulus intensity from the maximum ($8.5 \times 10^{17}$ photons/cm²/s).

The dopamine D2-like receptor antagonist eticlopride displays a greater selectivity than sulpiride for D2 and D3 receptors over D4 receptors (Patel et al., Neuropharmacology 44: 1038-1046, 2003). The effects of eticlopride (1 µM) were examined on 6 P23H rat RGCs that were stimulated with a spot of light. All cells showed an increase in light sensitivity upon application of eticlopride to the retina (FIG. 7A). On average, eticlopride increased light sensitivity of the cells by 0.31 log unit (from −2.76 to −3.07 log units). The difference of the means was statistically significant (P=0.002; paired t-test).

Figure 7B:
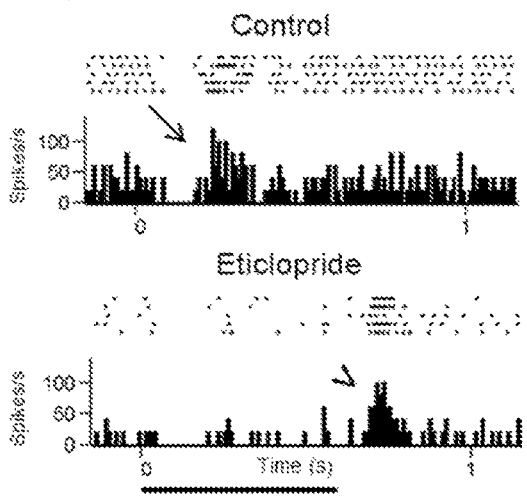
FIG. 7B shows the effects of 1 UM eticlopride on the light responses of a long-latency ON-center P23H rat RGCs. Spike raster plots and PSTHs of spike activity recorded from the RGC are displayed. Eticlopride eliminated the ON response (indicated by arrow) and brought out an OFF response (indicated by arrowhead). Horizontal bar indicates the timing and duration of the light stimulus.

FIG. 7B shows the effect of eticlopride on a long-latency ON-center P23H rat RGC. The RGC was stimulated with a small (250-µm diameter) spot of light. Timing and duration of the light stimulus is indicated by the horizontal line. The long-latency ON response (indicated by the arrow) to the small spot of light was abolished by eticlopride, and an OFF response (indicated by the arrowhead) appeared.

Example 7

5-HT2 Receptor Antagonists Improve Light Responses of RGCs

Experiments similar to those described in Example 1 were carried out on retinas isolated from P23H rats.

The 5-HT2 receptor antagonists MDL-100907 and SB-242084 were purchased from Tocris Bioscience (Minneapolis, MN). MDL-100907 is a 5-HT2A receptor antagonist (Kehne et al., J Pharmacol & Exp Ther 277: 968-981, 1996), whereas SB-242084 is a 5-HT2C receptor antagonist (Di Matteo, CNS Drug Reviews 6: 195-205, 2000). MDL-100907 was dissolved in a small amount of dimethylsulphoxide (DMSO) and diluted in physiological saline. SB-242084 was also dissolved in a small amount of dimethylsulphoxide (DMSO) and diluted in physiological saline. As in Example 1, the drug solutions were applied to the bathing solution using calibrated syringe pumps (Razel Scientific Instruments). Drugs were bath applied for ~10 min to ensure stable responses before effects were examined. Only one cell was studied in each retina to avoid possible residual drug effects.

Figure 8A:
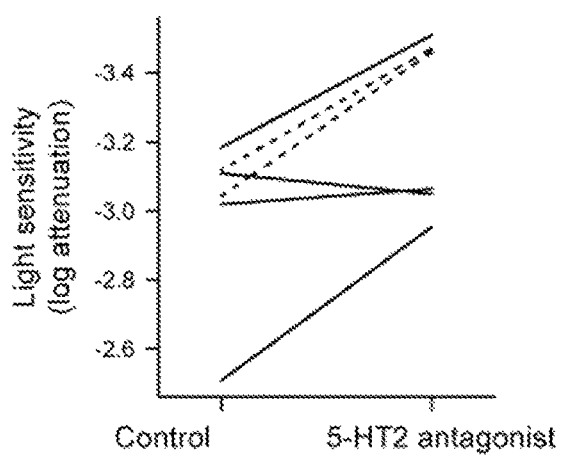
FIG. 8A shows data illustrating 5-HT2 antagonist-induced change in light sensitivity of P23H rat RGCs (n=6). The lines connect individual RGCs before and during drug treatment. The solid lines show data obtained with the 5-HT2 antagonist MDL-100907. The dash lines show data obtained the 5-HT2 antagonist SB-242084. The ordinate is labeled as log-unit attenuation in stimulus intensity from the maximum ($8.5 \times 10^{17}$ photons/cm²/s).

FIG. 8A shows the effects of the 5-HT2 receptor antagonists MDL-100907 and SB-242084 on the light sensitivity of P23H rat RGCs. The solid lines show data obtained with MDL-100907. The dash lines show data obtained SB-242084. On average, these antagonists increased the sensitivity of the 6 P23H rat RGCs by 0.25 log unit (from −3.00 to −3.25 log units). The difference of the means was statistically significant (P=0.031; paired t-test).

Figure 8B:
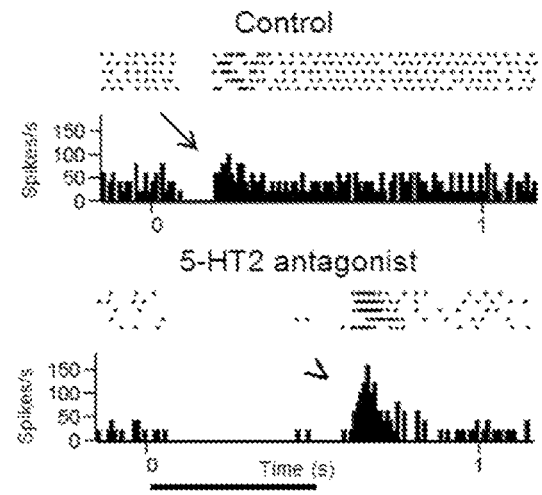
FIG. 8B shows the effects of the 5-HT2 receptor antagonist MDL-100907 (640 nM) on the light responses of a long-latency ON-center P23H rat RGC. Spike raster plots and PSTHs of spike activity recorded from the RGC are displayed. The 5-HT2 receptor antagonist eliminated the ON response (indicated by arrow) and brought out an OFF response (indicated by arrowhead). Horizontal bar indicates the timing and duration of the light stimulus.

FIG. 8B shows the effect of the 5-HT2 receptor antagonist MDL-100907 on the response of a long-latency ON-center P23H rat RGC to a flash of light. The long latency ON response (indicated by the arrow) to a small spot of light was abolished by MDL-100907, and an OFF response (indicated by the arrowhead) appeared.

Example 8

Methods of Improving Vision in a Subject with a Dopamine D2-Like Receptor Antagonist This example describes exemplary methods for improving vision in a subject with retinal degeneration. One of skill in the art will appreciate that methods that deviate from these specific methods can also be used to improve vision in a subject.

Subjects having a retinal degeneration (such as RP or AMD) are selected. In some cases, subjects are treated with an intravitreal sustained-release implant with eticlopride at a vitreal concentration of about 1 nM to 20 µM. In other cases, subjects receive intraocular injections of about 1 ng to 20 µg eticlopride one to three times per week.

Subjects are assessed for measures of visual function (such as visual acuity, visual field, contrast sensitivity, color vision, visual search, light/dark adaptation, and Amsler grid eye test) prior to initiation of therapy, periodically during the period of therapy, and/or at the end of the course of treatment. Subjects are also assessed for measures of retinal function (such as electroretinography (ERG; including multifocal and pattern ERGs), electrooculography (EOG), visual evoked potential (VEP), optical coherence tomography (OCT), fundus examination, or fluorescein angiography), prior to initiation of therapy, periodically during the period of therapy and/or at the end of the course of treatment.

The effectiveness of eticlopride therapy to improve visual function in a subject can be demonstrated by a decrease in detectable light intensity threshold, a reduction in a visual field defect, or an increase in contrast sensitivity, for example, compared to a control, such as an untreated subject, a subject with retinal degeneration prior to treatment (for example, the same subject prior to treatment), or a subject with the same retinal degeneration treated with placebo (e.g., vehicle only).

Example 9

Methods of Improving Vision in a Subject with a 5-HT2 Receptor Antagonist

This example describes exemplary methods for improving vision in a subject with retinal degeneration. One of skill in the art will appreciate that methods that deviate from these specific methods can also be used to improve vision in a subject.

Subjects having a retinal degeneration (such as RP or AMD) are selected. In some cases, subjects are treated with eye drops loaded with the 5-HT2 receptor antagonist MDL-100907 in the affected eye(s) 2-4 times daily for MDL-100907 to reach the back of the eye at a concentration of about 1 nM to 10 µM.

Subjects are assessed for measures of visual function (such as visual acuity, visual field, contrast sensitivity, color vision, visual search, light/dark adaptation, and Amsler grid eye test) prior to initiation of therapy, periodically during the period of therapy, and/or at the end of the course of treatment. Subjects are also assessed for measures of retinal function (such as electroretinography (ERG; including multifocal and pattern ERGs, electrooculography (EOG), visual evoked potential (VEP), optical coherence tomography (OCT), fundus examination, or fluorescein angiography), prior to initiation of therapy, periodically during the period of therapy and/or at the end of the course of treatment.

The effectiveness of MDL-100907 therapy to improve visual function in a subject can be demonstrated by a decrease in detectable light intensity threshold, a reduction in a visual field defect, or an increase in contrast sensitivity, for example, compared to a control, such as an untreated subject, a subject with retinal degeneration prior to treatment (for example, the same subject prior to treatment), or a subject with the same retinal degeneration treated with placebo (e.g., vehicle only).

Example 10

Methods of Improving Vision in a Subject with an Antipsychotic Drug

This example describes exemplary methods for improving vision in a subject with retinal degeneration. One of skill in the art will appreciate that methods that deviate from these specific methods can also be used to improve vision in a subject.

Subjects having a retinal degeneration (such as RP or AMD) are selected. In some cases, subjects are treated with Clozaril® beginning with one-half of a 25 mg tablet (12.5 mg) once or twice daily and then continued with daily dosage increments of 25-50 mg/day, if well-tolerated, to achieve a target dose of 300-450 mg/day by the end of 2 weeks.

Subjects are assessed for measures of visual function (such as visual acuity, visual field, contrast sensitivity, color vision, visual search, light/dark adaptation, and Amsler grid eye test) prior to initiation of therapy, periodically during the period of therapy, and/or at the end of the course of treatment. Subjects are also assessed for measures of retinal function (such as electroretinography (ERG; including multifocal and pattern ERGs, electrooculography (EOG), visual evoked potential (VEP), optical coherence tomography (OCT), fundus examination, or fluorescein angiography), prior to initiation of therapy, periodically during the period of therapy and/or at the end of the course of treatment.

The effectiveness of Clozaril® therapy to improve visual function in a subject can be demonstrated by a decrease in detectable light intensity threshold, a reduction in a visual field defect, or an increase in contrast sensitivity, for example, compared to a control, such as an untreated subject, a subject with retinal degeneration prior to treatment (for example, the same subject prior to treatment), or a subject with the same retinal degeneration treated with placebo (e.g., vehicle only).

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. A method for treating a retinal disorder in a subject, the method comprising administering to the subject a therapeutically effective amount of a compound selected from benperidol, droperidol, fluanisone, haloperidol, moperone, pipamperone, trifluperidol, chlorpromazine, prochlorperazine, fluphenazine, trifluoperazine, perphenazine, acetophenazine, carphenazine, triflupromazine, mesoridazine, thioridazine, thiothixene, chlorprothixene, loxapine, molindone, pimozide, clozapine, risperidone, olanzapine, setindole, sulpiride, amisulpride, zuclopenthixol, aripiprazole, quetiapine, ziprasidone, zotepine, paliperidone, olanzapine, melperone, lurasidone, iloperidone, blonanserin, asenapine, eticlopride, remoxipride, (R)-(+)-α-(2,3-dimethoxyphenyl)-[1-[2-(4-fluorophenyl)ethyl]-4-piperinemethanol, 6-chloro-2,3-dihydro-5-methyl-N-[6-[(2-methyl-3-pyridinyl)oxy]-3-pyridinyl]-1H-indole-1-carboxyamide dihydrochloride, and 3-(4-[4-chlorophenyl]piperazin-1-yl)-methyl-1H-pyrrolo[2,3-b]pyridinetrihydrochloride.

2. The method of claim 1, wherein said retinal disorder is selected from the group consisting of macular degeneration, diabetic retinopathy, age-related macular degeneration, macular edema, and retinitis pigmentosa.

3. The method of claim 1, wherein said subject is a mammal.

4. The method of claim 3, wherein said subject is a human.

5. The method of claim 1, further comprising administering said compound in combination with a pharmaceutically acceptable carrier.

6. The method of claim 5, wherein the said pharmaceutically acceptable carrier is suitable for administration to the eye.

7. The method of claim 1, wherein said retinal disorder is a retinal degeneration.

8. The method of claim 1, wherein said compound is selected from sulpiride, amisulpiride, eticlopride, and 3-(4-[4-chlorophenyl]piperazin-1-yl)-methyl-1H-pyrrolo[2,3-b]pyridinetrihydrochloride.

9. The method of claim 8, wherein said compound is sulpiride.

10. The method of claim 9, wherein sulpiride is (−)-sulpiride.

11. The method of claim 1, wherein said compound is selected from (R)-(+)-α-(2,3-dimethoxyphenyl)-[1-[2-(4-fluorophenyl)ethyl]-4-piperinemethanol and 6-chloro-2,3-dihydro-5-methyl-N-[6-[(2-methyl-3-pyridinyl)oxy]-3-pyridinyl]-1H-indole-1-carboxyamide dihydrochloride.

12. The method of claim 1, wherein administering is via intraocular administration.

13. The method of claim 1, wherein administering is via systemic administration.

14. A method for treating a retinal disorder in a subject, the method comprising administering to the subject a therapeutically effective amount of a compound selected from sulpiride, amisulpride, eticlopride, (R)-(+)-α-(2,3-dimethoxyphenyl)-[1-[2-(4-fluorophenyl)ethyl]-4-piperinemethanol, 6-chloro-2,3-dihydro-5-methyl-N-[6-[(2-methyl-3-pyridinyl)oxy]-3-pyridinyl]-1H-indole-1-carboxyamide dihydrochloride, and 3-(4-[4-chlorophenyl]piperazin-1-yl)-methyl-1H-pyrrolo[2,3-b]pyridinetrihydrochloride.

15. The method of claim 14, wherein said retinal disorder is a retinal degeneration.

16. The method of claim 14, wherein said retinal disorder is selected from the group consisting of macular degeneration, diabetic retinopathy, age-related macular degeneration, macular edema, and retinitis pigmentosa.

17. The method of claim 14, wherein said compound is selected from sulpiride, amisulpiride, eticlopride, and 3-(4-[4-chlorophenyl]piperazin-1-yl)-methyl-1H-pyrrolo[2,3-b]pyridinetrihydrochloride.

18. The method of claim 14, wherein said compound is selected from (R)-(+)-α-(2,3-dimethoxyphenyl)-[1-[2-(4-fluorophenyl)ethyl]-4-piperinemethanol and 6-chloro-2,3-dihydro-5-methyl-N-[6-[(2-methyl-3-pyridinyl)oxy]-3-pyridinyl]-1H-indole-1-carboxyamide dihydrochloride.

19. The method of claim 14, wherein administering is via intraocular administration.

20. The method of claim 14, wherein administering is via systemic administration.

* * * * *